United States Patent [19]

Hounsfield

[11] 4,160,911
[45] Jul. 10, 1979

[54] FAN BEAM CT APPARATUS THE INTERBEAM ANGLE OF WHICH VARIES WITH POSITION ACROSS THE FAN

[75] Inventor: Godfrey N. Hounsfield, Newark, England

[73] Assignee: E M I Limited, Hayes, England

[21] Appl. No.: 778,578

[22] Filed: Mar. 17, 1977

[30] Foreign Application Priority Data

Mar. 18, 1976 [GB] United Kingdom ............... 11026/76

[51] Int. Cl.² .............................................. A61B 6/02
[52] U.S. Cl. .................................. 250/445 T; 250/360
[58] Field of Search ............ 250/320, 360, 366, 445 T

[56] References Cited

U.S. PATENT DOCUMENTS 3,973,128  8/1976  Lemay ............................ 250/445 T

*Primary Examiner*—Alfred E. Smith
*Assistant Examiner*—T. N. Grigsby

*Attorney, Agent, or Firm*—Cooper, Dunham, Clark, Griffin & Moran

[57] ABSTRACT

A computerized tomographic apparatus is described in which the source produces a fan-shaped distribution of X-rays and the detectors extend across the distribution so as to respectively receive radiation propagated along different beams of the distribution. The source and detectors are rotated around a patient about an axis intersecting a desired cross-sectional slice of the patient. The beam paths, through the body slice, along which radiation is projected for any one source position are divergent, but output signals relating to the totality of beam paths irradiated during a considerable rotational movement of the source around the body can be sorted into sets relating to parallel beam paths, to assist in processing them. However the sets of paths exhibit non-uniformity of spacing which can cause difficulty if convolution processing is employed. In order to reduce or overcome this problem, the present invention provides that the spacing between adjacent beams varies across the distribution.

5 Claims, 3 Drawing Figures

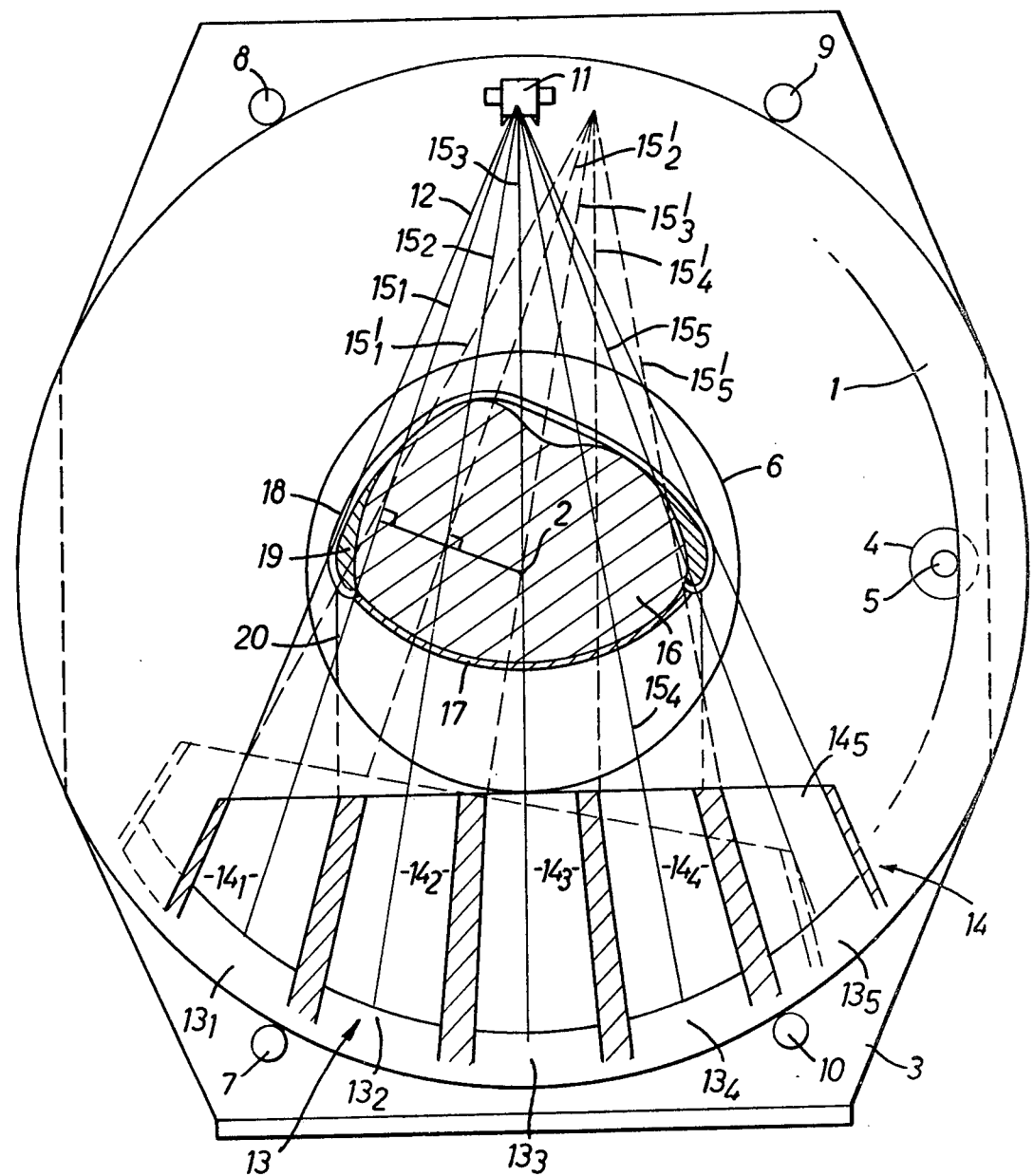

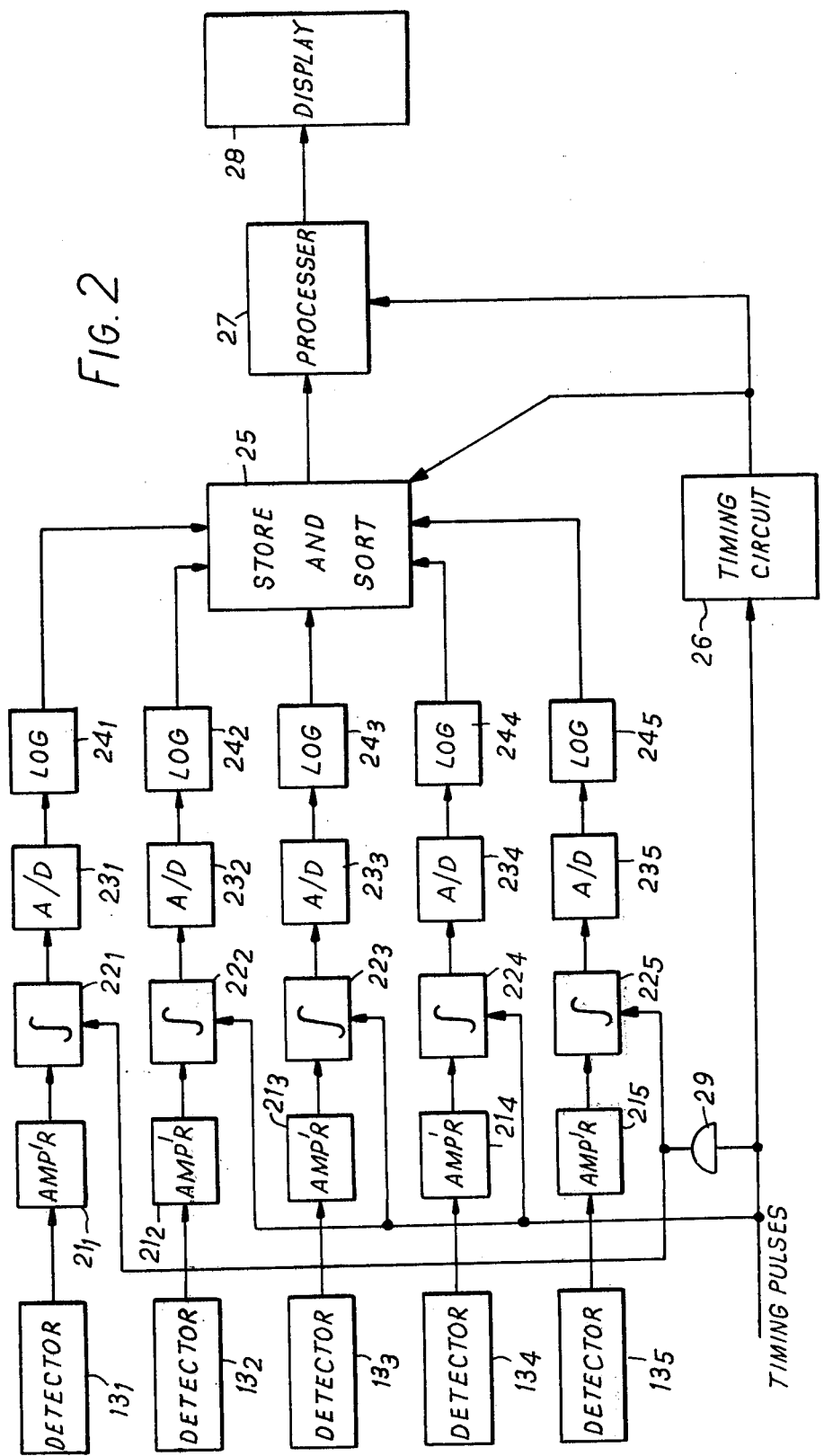

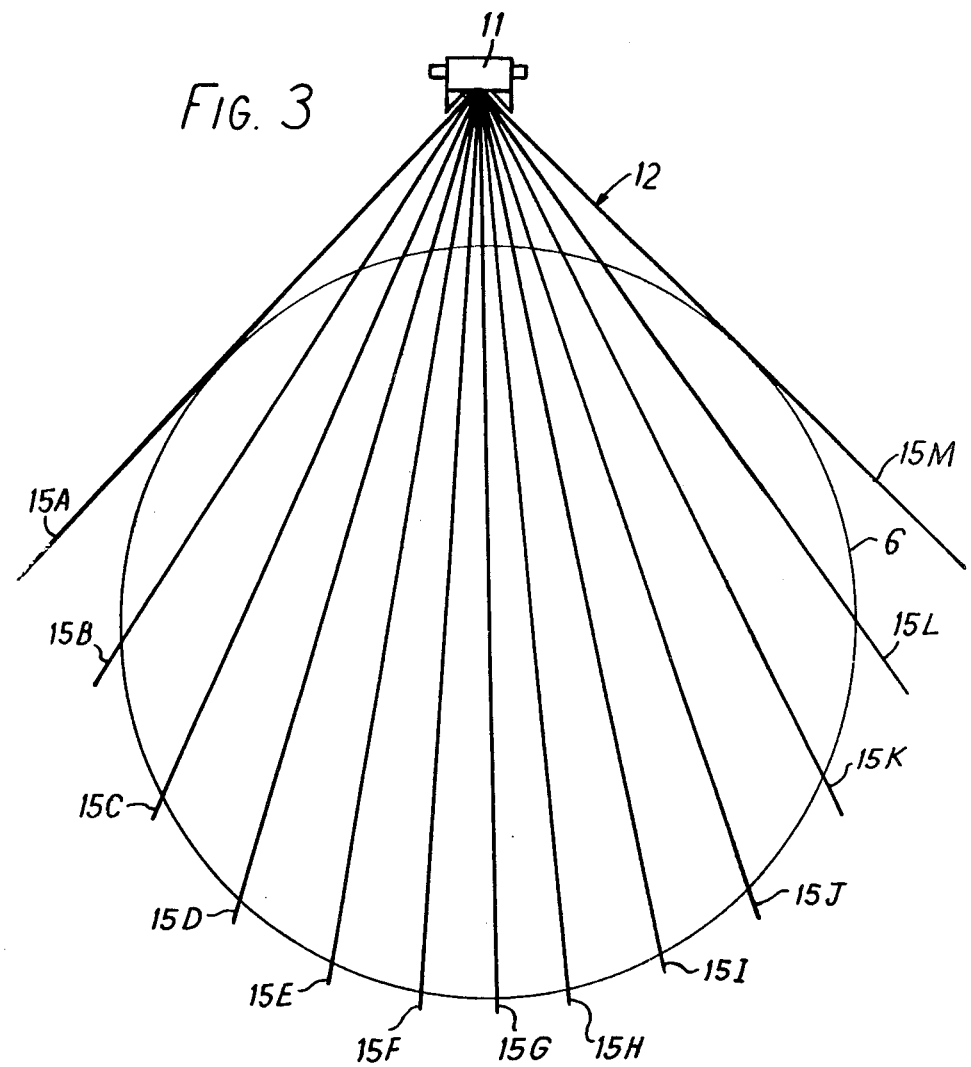

FAN BEAM CT APPARATUS THE INTERBEAM ANGLE OF WHICH VARIES WITH POSITION ACROSS THE FAN

The present invention relates to radiography, and it relates more particularly to that branch of radiography which has become known as computerised axial tomography, or briefly C.A.T. Apparatus for performing C.A.T. has the aim of producing a representation of the absorption coefficients, with respect to penetrating radiation, at a plurality of elemental locations distributed over a cross-sectional slice of a body under investigation. Such apparatus is disclosed and claimed in U.S. Pat. No. 3,778,614.

The technique of performing C.A.T. involves deriving signals indicative of the absorption suffered by penetrating radiation, such as X-radiation, on traversing many beam paths through the slice of the body. These signals are then processed to evaluate the aforementioned coefficients.

In order that the radiation may be projected through the slice along the many beam paths referred to above, it is usual to mount a source of the radiation and one or more detectors sensitive to the radiation at opposite sides of the body and to scan one or both of these components relative to the body in the plane of the region. The scanning may comprise a combination of translational and rotational scanning movements, both effected mechanically. If, however, it is desired to obtain the signals rapidly, the mechanical scanning may comprise only a rotational scanning movement, and in these circumstances the X-ray tube is arranged to generate a substantially planar, fan-shaped distribution of the radiation, the angle of the fan being sufficient to irradiate at least a substantial part of the slice; the plane of the fan, of course, being aligned with the slice. An array of detectors is provided, the detectors being distributed across the breadth of the distribution of radiation so that each receives radiation projected along a respective beam within the distribution; the beams being equiangularly spaced. As the source and the detectors are rotated relative to the body, each detector is repeatedly sampled at intervals which correspond to rotational movements corresponding to the inter-beam angle, and by this means a sequence of signals indicative of the absorption suffered by the radiation on traversing each of a group of beam paths is derived from each detector. The group of beam paths to which the signals derived from any one detector relate will not, of course, be parallel to one another; they will be inclined to one another at substantially the aforementioned inter-beam angle. Such a group of beam paths will, however, be characterised by having a common perpendicular distance to the axis of the rotational scan, which axis is usually substantially perpendicular to the slice (and thus of the distribution of radiation) and passes through the body under examination.

It is convenient to process the signals derived from all of the detectors by means of the technique described and claimed in U.S. Pat. No. 3,924,129, but this technique is best applied to output signals relating to sets of equally spaced, parallel beam paths.

The signals obtained as described above can be sorted into sets relating to parallel beam paths; it being appreciated that the signals of a set are all derived from different detectors and obtained at different times during the scanning. However these beam paths are not equally spaced and when it is desired to evaluate the aforementioned coefficients with high accuracy, it has been found necessary to allow for this lack of equal spacing, which arises because the perpendicular distances to the axis of rotation for the beams received by the various detectors vary in a substantially sinusoidal fashion from the axis outwards; the paths being more closely spaced towards the edges of the region of interest than they are at the centre thereof.

The object of this invention is to allow for the aforementioned inequality of beam spacing.

According to this invention there is provided computerised tomographic apparatus including a source of a fan-shaped distribution of penetrating radiation, such as X-radiation, support means supporting said source so that said radiation propagates across a location at which a desired cross-sectional slice of a patient's body can be disposed, detector means, including a plurality of detector devices, supported by said support means and disposed to receive radiation, propagated along respective beams within said distribution, after it has traversed said location, scanning means for causing said support means, and with it said source and said detector means, to move angularly around said location causing, on the one hand, said source to irradiate said location from a plurality of angularly spaced positions therearound and, on the other hand, the detector means to receive radiation traversing said location from each of said positions, and wherein the angle between adjacent ones of said beams varies across said distribution.

In order that the invention may be clearly understood and readily carried into effect, some embodiments thereof will now be described with reference to the accompanying drawings, of which:

FIG. 1 shows, in front elevational view, some of the components of a C.A.T. apparatus in which the only mechanical scanning movement is a rotational one, and shows how the aforementioned non-uniformity of spacing of parallel beam paths occurs, FIG. 2 shows a block diagrammatic circuit diagram indicating how the data produced by the apparatus shown in FIG. 1 can be processed, and FIG. 3 shows, in schematic form and on an exaggerated scale, a variation of angle between adjacent paths with position across a fan-shaped distribution of radiation.

Referring now to FIG. 1, a ring-like rotatable support structure 1, is mounted for rotation about an axis 2. The structure 1 comprises an annular member which can be rotated relative to a static main frame 3 by an electric motor 4. The motor 4 is mounted on the main frame 3 and drives a gear wheel 5 which co-operates with gear teeth (not shown) formed all around the inner periphery of the ring-like structure 1. The main frame 3 has an aperture 6 formed therein, the apetture 6 being concentric with the ring-like structure 1, and also supports a number of guides 7, 8, 9, 10 which act as bearings during rotation of structure 1 about the axis 2 and thus support the load of that structure; the guides 7 through 10 being also formed with flanges to limit fore-and-aft movement of the structure 1.

The structure 1 supports an X-ray tube 11, arranged to produce a planar fan-shaped distribution 12 of X-radiation, and a bank 13 of detectors, the detectors being sensitive to said radiation and being distributed across the breadth of the distribution 12. The individual detectors, which may comprise thalluim-activated sodium iodide crystals, are numbered $13_1, 13_2 \ldots 13_5$; only five detectors being shown in this case for clarity, although more typically, for a fan-shaped distribution of angle 40° as shown, 120 detectors would be used, adjacent detectors being angled at ⅓° to each other. Each detector in the array 13 views the radiation source 11 through a respective collimator 14 so as to reduce the amount of scattered radiation received by the detectors and thus each detector receives radiation along a respective beam 15 in the distribution 12; the beams being indicated in the drawing by their centre lines, although it will be appreciated that the beams are actually of finite width as determined by the collimator dimensions. It will also be appreciated that, prior to its incidence upon the collimators 14, the distribution 12 is continuous across its breadth, although this need not necessarily be the case and the distribution could be sectioned up into beams before being incident on the body.

The body 16 to be examined is supported on a bed 17 and held firmly thereon by means of a strap 18 secured to the sides of the bed. Packing material 19 is inserted in gaps between the body and the bed in order to reduce, so far as is possible, the entrapment of air between the patient and the bed. The material 19 is preferably contained in one or more flexible bags and absorbs the radiation to an extent similar to human body tissue. The bed is supported on either side of the main frame 3; one of the supports being shown at 20. It will be appreciated, of course, that the aperture 6 in the main frame 3 must be sufficiently large to enable the body 16 to be positioned as required relative to the distribution 12.

As will be seen, when the structure 1 is in the position shown in the drawing, so that the source 11 projects the distribution 12 of radiation through the body from the direction indicated in solid lines, each of the beams 15 traverses a respective path through the body 16, and the corresponding detector 13 provides an output signal indicative of the absorption suffered by the radiation on traversing the relevant path. In practice, an output signal relates not to a beam path as irradiated from a single point, but to a broader beam path irradiated during rotation of the structure 1 through a finite angle. This matter, however, will be ignored henceforth, because it is not relevant to the understanding of the invention, and it will be assumed that the output signals relate to beam paths irradiated at unique angular positions of the structure 1.

It will be observed that the various beams 15, and consequently the corresponding beam paths through the body, diverge from one another at equal angles and so the group of output signals obtained in any one position of the structure 1 do not relate to a parallel set of beam paths.

If the structure 1 is rotated through an angle corresponding to the angle between adjacent beams 15, so that the distribution 12 assumes the position indicated by dotted lines, then the beams 15 will irradiate a new group of beam paths through the body 16. In this case, the beam path $15_2'$, viewed by detector $13_2$ from its new position is parallel with the beam path $15_1$ which was viewed by detector $13_1$ in its original position. Likewise the path $15_3'$ viewed by detector $13_3$ in its new position is parallel to the path $15_2$ viewed by detector $13_2$ in its original position, and so on. Further rotational movement of the structure 1 about the axis 2 causes various of the detectors to provide output signals relating to beam paths parallel to paths for which output signals have previously been provided by other detectors.

As the mechanical movement is purely rotational, however, the beam paths of a parallel set are not uniformly spaced across the irradiated region of the body. This can be seen by comparing the perpendicular distance from the axis 2 to two parallel beam paths as irradiated by beams $15_1$ (detected by detector $13_1$) and $15_2'$ (detected by detector $13_2$), the structure 1 having rotated through an angle corresponding to the inter-beam angle between the irradiation of the two beam paths. If the distance from the point source of X-rays, within tube 11, to the axis 2 is designated r, and if the inter-beam angle is 10°, then the perpendicular distances from axis 2 to beams $15_1$ and $15_2'$ respectively are r sin 20° and r sin 10° respectively. Since the third beam of the parallel set in question will pass through the axis 2 and be detected by detector $13_3$ after the structure 1 has rotated through a further 10°, it will be seen that the values r sin 10° and r (sin 20°−sin 10°) represent the distances between respective pairs of beam paths in a parallel set and that these distances are not equal. Clearly the same thing will happen for beam paths on the other side of the axis 2 to those irradiated by beams $15_1$ and $15_2'$, and clearly also the non-uniformity of distance will be the same for all parallel sets of beam paths. If it is desired to use a processing technique of the kind described and claimed in the aforementioned U.S. Pat. No. 3,924,129, and if it is desired to evaluate the aforementioned absorption coefficients with high accuracy, this departure from uniformity must be allowed for.

In accordance with this example of the invention, the various beams $15_1$, $15_2$ etc. are not equi-angularly spaced as shown in FIG. 1. Instead, they are spaced in angle so as to cause the beam paths irradiated thereby, on rotation of the member 1, to conform to uniformly spaced, parallel sets.

This can be achieved, for example, by progressively increasing the angle between adjacent beams in moving away from the centre beam of the fan ($15_3$) so as to make the spacing of adjacent beam paths of a parallel set conform to r sin 10°. For example, in the arrangement shown in FIG. 1 it would be necessary, in order to achieve this end, to make the angular spacing between beam $15_3$ and beam $15_5$ 20.4° instead of 20° as in FIG. 1; the angular spacing between beams $15_3$ and $15_4$ remaining at 10°. FIG. 3 shows, in schematic form and on an exaggerated scale, a variation of angular spacing between adjacent beams with position across fan-shaped distribution of radiation. The center-lines of the beams are shown at $15_A$ through through $15_M$, and the distribution of radiation is shown at 12, having its origin at a source 11. The aperture 6 referred to in FIG. 1 is also shown.

It will be evident that instead of equalising the spacing of adjacent beam paths of a parallel set by increasing the angular spacing between beams in moving away from the centre of the fan, of radiation, the converse arrangement, namely decreasing the angular spacing between adjacent beams in moving from an edge of the fan into the centre thereof could be adopted.

In either event account has to be taken of the fact that, because the beams are no longer equi-angularly spaced, it is difficult to establish sets of output signals relating to parallel beam paths. This difficulty can be overcome by suitably strobing the output signals as derived from the various detectors so that the output signals are obtained from different detectors at slightly different times. An alternative approach is to simultaneously sample the output signals derived from all of the detectors with a timing which is a compromise between the timing which is actually required for beams disposed centrally of the fan and that actually required for beams disposed towards the periphery of the fan.

Referring now to FIG. 2, some circuits connected to the detectors $13_1$ to $13_5$ are shown in block diagrammatic form.

Detector $13_1$ feeds an amplifier $21_1$ and thence an integrator $22_1$, an analogue-to-digital converter circuit $23_1$ and a logarithmic converter circuit $24_1$. Likewise detectors $13_2$ through $13_5$ feed respective circuits identified by the same reference numerals as those associated with detector $13_1$, but having respective suffices appropriate to the detectors concerned.

The logarithmic converter circuits $24_1$ through $24_5$ feed a digital store 25, the data being written into and read out of the store in such a way as to reassemble the data into sets relating to parallel beam paths. To this end, the store 25 contains a storage address for each beam paths, the addresses being conveniently arranged in rows and columns such that each row is characterised by a particular angular disposition of beam paths and the columns are characterised by respective distances of beam paths from the axis 2 of rotation of the system.

The data are written into the store 25 and read out therefrom under the control of timing signals derived from a master timing circuit 26 which itself receives timing impulses, indicative of the progress of the rotational scanning movement of the member 1 and derived from a graticule and photodetector arrangement of known kind (not shown) suitably disposed in relation to the member 1 as will be evident to those skilled in the art.

The data are written into the store 25 as they are derived, and are deposited into the appropriate addresses, and they are read out a row at a time and applied to a processing circuit 27 which can conveniently be of the form described in U.S. Pat. No. 3,924,129; the disclosure of which is incorporated herein by reference. Once the processing has been effected, a repesentation of the variation of absorption coefficient, with respect to the radiation, over the body slice is produced by any suitable means 28, such as a tone printer, a cathode ray tube or an electrostatic printer.

The timing pulses applied to the master timing circuit 26 are also used to periodically read and reset the integrator circuits $22_1$ through $22_5$, so as to enable output signals relating to individual beam paths to be distinguished from one another. The pulses applied to the integrator circuits $22_2$ through $22_4$ are synchronous with one another, but those applied to the integrators $22_1$ and $22_5$ are delayed, in a delay component 29 of any suitable kind, by an amount sufficient for the member 1 to rotate through a further 0.4° so that the integrator $22_1$ and $22_5$ produce signals relating to beam paths which can be assimulated into parallel sets at the desired angles and are, moreover, such that the beam paths of each set are substantially uniformly spaced.

In a practical system using more detectors, the detectors may be considered in pairs disposed at equal angles on either side of the median line of the fan-shaped distribution 12 of radiation, and the integrators associated with each pair of detectors are read and reset by timing pulses subjected to a unique delay. The delay, of course, increases with increasing angular displacement of the detector pairs from the aforementioned median line.

What I claim is:

1. Computerised tomographic apparatus including a source of a fan-shaped distribution of penetrating radiation, such as X-radiation, support means supporting said source so that said radiation propagates across a location at which a desired cross-sectional slice of a patient's body can be disposed, detector means, including a plurality of detector devices, supported by said support means and disposed to receive radiation, propagated along respective beams within said distribution after it has traversed said location, scanning means for causing said support means, and with it said source and said detector means, to move angularly around said location causing, on the one hand, said source to irradiate said location from a plurality of angularly spaced positions therearound and, on the other hand, the detector means to receive radiation traversing said location from each of said positions, and wherein the angle between adjacent ones of said beams varies across said distribution to cause substantially uniform spacing of beams which are substantially parallel to each other.

2. Apparatus according to claim 1 wherein said detector means produces output signals indicative of radiation received thereby and means are provided for sampling said output signals so that they relate to identifiable beam paths across said location.

3. Apparatus according to claim 2 wherein all of said detector devices are synchronously sampled at times relating to angular movement of said support means through an angle corresponding substantially to the mean of the angles between all of said adjacent beams.

4. Apparatus according to claim 2 including strobing circuit means for sampling said detector devices in pairs at respective times selected to allow for said variation in the angle between adjacent ones of said beams.

5. Apparatus according to claim 1 wherein the scanning means moves said source about an axis and the angle between adjacent beams of said fan-shaped distribution of penetrating radiation increases in moving from the center of the distribution toward its sides such that the difference between the distances of each pair of adjacent beams from the axis is about the same.

* * * * *